(12) United States Patent
Bley et al.

(10) Patent No.: US 7,915,456 B2
(45) Date of Patent: Mar. 29, 2011

(54) SALTS OF STYPHNIC ACID

(75) Inventors: Ulrich Bley, Furth (DE); Rainer Hagel, Erlangen (DE); Aleksej Hoschenko, Furth (DE); Peter Simon Lechner, Oberasbach (DE)

(73) Assignee: Raug Ammotec GmbH, Furth (DE)

( * ) Notice: Subject to any disclaimer, the term of this patent is extended or adjusted under 35 U.S.C. 154(b) by 0 days.

(21) Appl. No.: 12/158,367

(22) PCT Filed: Dec. 18, 2006

(86) PCT No.: PCT/EP2006/069846
§ 371 (c)(1),
(2), (4) Date: Jun. 20, 2008

(87) PCT Pub. No.: WO2007/071649
PCT Pub. Date: Jun. 28, 2007

(65) Prior Publication Data
US 2009/0005607 A1    Jan. 1, 2009

(30) Foreign Application Priority Data

Dec. 20, 2005 (DE) .................. 10 2005 061 324

(51) Int. Cl.
*C07C 205/06* (2006.01)
*C06C 7/00* (2006.01)
(52) U.S. Cl. ........................................ 568/710; 102/204
(58) Field of Classification Search ................. 568/710; 102/204
See application file for complete search history.

(56) References Cited

U.S. PATENT DOCUMENTS 2,969,638 A * 1/1961 Sammons ...................... 60/219
4,412,492 A * 11/1983 Knights et al. ................ 102/204

FOREIGN PATENT DOCUMENTS

| DE | 26 40 799 | 9/1976 |
|---|---|---|
| DE | 41 17 719 | 12/1992 |
| DE | 100 09 685 | 10/2000 |
| WO | WO 99/48842 | 9/1999 |

* cited by examiner

*Primary Examiner* — Sikarl A Witherspoon
(74) *Attorney, Agent, or Firm* — Antonelli, Terry, Stout & Kraus, LLP.

(57) ABSTRACT

The invention relates to the salts of styphnic acid, to methods for producing the same and to their use.

19 Claims, No Drawings

SALTS OF STYPHNIC ACID

The present invention concerns salts of styphnic acid, a process for their preparation and their use.

Conventional primer substances, which are used for example in vehicle safety systems, have the disadvantage that, owing to low decomposition temperatures, they cannot be used in the engine compartment of motor vehicles. In the engine compartment of a motor vehicle, temperatures of 140° C. and more are reached, which requires a decomposition temperature of a primer substance of over 300° C. Potassium dinitrobenzofuroxanate, for example, has a decomposition temperature of approx. 220° C. and is therefore unsuitable for this purpose.

The object of the present invention was to provide a substance which is suitable as a primer substance and which overcomes the disadvantages of the prior art. Further objects consisted in providing a primer substance having a decomposition temperature of over 300° C., which is free from heavy metals, is suitable for both mechanical and electrical ignition systems, can be used e.g. in vehicle safety systems, ammunition and propellant cartridges for powder actuated tools, and/or the preparation of which is possible by simple industrial processes.

According to the invention, these objects are surprisingly achieved by the features of claims 1, 4, 11 and 12. Preferred embodiments are found in the subclaims.

Surprisingly, it has been found that these objects are achieved by the alkali salts and alkaline-earth salts of styphnic acid (2,4,6-trinitro-1,3-dihydroxybenzene) according to the invention—referred to below as styphnates for short—the preparation thereof and their use according to the invention.

Preferred according to the invention as primer substance are potassium styphnate, calcium styphnate and their mixed salt potassium-calcium styphnate. Particularly preferred according to the invention are basic calcium styphnate and basic potassium-calcium styphnate.

The preparation of the primer substance according to the invention is achieved starting from an aqueous magnesium styphnate solution:
- in the case of the preparation of potassium styphnate, by precipitation from the magnesium styphnate solution by the addition of potassium nitrate;
- in the case of the preparation of calcium styphnate, by precipitation from the magnesium styphnate solution by the addition of calcium nitrate; basic calcium styphnate is formed when alkali hydroxides are added to a calcium styphnate suspension;
- in the case of the preparation of potassium-calcium styphnate, by precipitation from potassium styphnate solution with stoichiometric addition of calcium nitrate; basic potassium-calcium styphnate is formed when alkali hydroxides are added to a potassium-calcium styphnate suspension.

These styphnates can be used according to the invention as a primer substance both individually and in a mixture with one another and/or optionally in a mixture with the conventional additives, such as e.g. oxidising agents, reducing agents, sensitising agents, binders, high-energy additives and combustion modifiers and processing auxiliaries.

The following may be employed according to the invention as additives when the substances according to the invention are used as a primer substance, e.g. in ignition systems:
1. Oxidising agents (individually or in mixtures):
    Nitrates of alkali metals or alkaline-earth metals or of ammonium, such as sodium nitrate or potassium nitrate, perchlorates of alkali metals or alkaline-earth metals or of ammonium, peroxides of alkaline-earth metals or of zinc, preferably zinc peroxide.
2. Reducing agents (individually or in mixtures):
    Aluminium, titanium, titanium hydride, boron, boron hydride, zirconium, zirconium hydride, silicon, graphite, activated carbon, carbon black, preferably titanium.
3. Sensitising agents (individually or in mixtures):
    Tetrazene, potassium dinitrobenzofuroxanate, diazodinitrophenol.
4. Binders (individually or in mixtures):
    Adhesin, cellulose and derivatives thereof, polyvinyl butyrals, polynitropolyphenylene, polynitrophenyl ether, Plexigum, polyvinyl acetate and copolymers, preferably adhesin.
6. High-energy additives (individually or in mixtures):
    Hexogen, octogen, nitropenta and nitrocellulose.
7. Combustion modifiers and processing auxiliaries (individually or in mixtures):
    Nitrocellulose ball powder, acetonyl acetates, salicylates, silicates, silica gels, boron nitride, preferably nitrocellulose ball powder.

When the substances according to the invention are used as a primer substance, this is distinguished by freedom from heavy metals, high thermal stability and, in the case of calcium styphnate and potassium-calcium styphnate, by the content of calcium, which is advantageous for weapons systems through the formation of calcium carbonate in the combustion residues, owing to the favourable tribological properties of calcium carbonate. The decomposition temperatures of the styphnates according to the invention are approx. 335° C. The primer substance can be ignited both mechanically and electrically.

In detail, the present invention provides:
- an alkali salt and/or alkaline-earth salt of styphnic acid as a primer substance, this being potassium styphnate, calcium styphnate and their mixed salt potassium-calcium styphnate, preferably basic calcium styphnate and basic potassium-calcium styphnate;
- a potassium-calcium styphnate which contains 10 to 15, preferably 12 to 14 wt. % potassium and 5 to 10, preferably 6 to 8 wt. % calcium;
- a basic potassium-calcium styphnate which contains 10 to 15, preferably 11 to 13 wt. % potassium and 10 to 15, preferably 11 to 13 wt. % calcium;
- a process for the preparation of potassium styphnate by precipitation from aqueous magnesium styphnate solution by the addition of potassium nitrate;
- a process for the preparation of calcium styphnate by precipitation from aqueous magnesium styphnate solution by the addition of calcium nitrate;
- a process for the preparation of basic calcium styphnate by the addition of alkali hydroxides to a calcium styphnate suspension;
- a process for the preparation of potassium-calcium styphnate by precipitation from potassium styphnate solution by the addition of calcium nitrate, preferably by the stoichiometric addition of calcium nitrate;
- a process for the preparation of basic potassium-calcium styphnate by the addition of alkali hydroxides to a potassium-calcium styphnate suspension;
- the use of alkali salts and/or alkaline-earth salts of styphnic acid and/or one or more mixed salts of alkali salts and/or alkaline-earth salts of styphnic acid as primer substances;
- the use of alkali salts and/or alkaline-earth salts of styphnic acid and/or one or more mixed salts of alkali salts and/or alkaline-earth salts of styphnic acid as a component of primer compositions, preferably as a primer substance in primer compositions;

the use of alkali salts and/or alkaline-earth salts of styphnic acid and/or one or more mixed salts of alkali salts and/or alkaline-earth salts of styphnic acid in ignition systems for vehicle safety systems, ammunition and/or propellant cartridges for bolt-driving tools;

the use of alkali salts and/or alkaline-earth salts of styphnic acid and/or one or more mixed salts of alkali salts and/or alkaline-earth salts of styphnic acid in ignition systems for vehicle safety systems, preferably in those which are used in the engine compartment of a motor vehicle;

the use of alkali salts and/or alkaline-earth salts of styphnic acid and/or one or more mixed salts of alkali salts and/or alkaline-earth salts of styphnic acid in ignition systems that are ignited electrically.

The invention is explained below by means of examples, without limiting the invention to the examples:

EXAMPLE 1

Potassium-Calcium Styphnate

Basic potassium-calcium styphnate, prepared by precipitation from potassium styphnate solution with the stoichiometric addition of calcium nitrate, was investigated by atomic absorption spectroscopy. The following proportions of potassium and calcium were found:

| | |
|---|---|
| Potassium: | approx. 13 wt. % |
| Calcium: | approx. 7 wt. % |

EXAMPLE 2

Basic Potassium-Calcium Styphnate

Potassium-calcium styphnate, prepared by the addition of alkali hydroxides to a potassium-calcium styphnate suspension, was investigated by atomic absorption spectroscopy. The following proportions of potassium and calcium were found:

| | |
|---|---|
| Potassium: | approx. 11.5 wt. % |
| Calcium: | approx. 12 wt. % |

Table 1 shows the decomposition temperatures, friction and impact sensitivities of the substances. The friction and impact sensitivities were measured by methods of the German Bundesanstalt für Materialforschung (BAM) [Federal Institute for Materials Research], while the decomposition temperatures were measured by thermogravimetric analysis (Mettler) at a rate of heating of 10° C. per minute.

TABLE 1

| | Potassium-calcium styphnate | Basic potassium-calcium styphnate | Basic calcium styphnate |
|---|---|---|---|
| Friction sensitivity in N | 9 | 9 | 9 |
| Impact sensitivity in J | 3 | 3 | 4 |
| Decomposition temperature in ° C. | 345 | 340 | 335 |

The invention claimed is:

1. A salt of styphnic acid, characterised in that it is selected from the group consisting of potassium-calcium styphnate, basic potassium-calcium styphnate and basic calcium styphnate and has a decomposition temperature of over 300° C.

2. The salt of styphnic acid according to claim 1, characterised in that the salt is potassium-calcium styphnate and contains 10 to 15 wt. % potassium and 5 to 10 wt. % calcium.

3. The salt of styphnic acid according to claim 1, characterised in that the salt is basic potassium-calcium styphnate and contains 10 to 15 wt. % potassium and 10 to 15 wt. % calcium.

4. The salt of styphnic acid according to claim 1 for use as a primer substance.

5. The salt of styphnic acid according to claim 1 for use as a primer substance in primer compositions.

6. The salt of styphnic acid according to claim 1 for use in ignition systems for vehicle safety systems, ammunition and/or propellant cartridges for powder actuated tools.

7. The salt of styphnic acid according to claim 1 for use in ignition systems for vehicle safety systems which are used in the engine compartment of a motor vehicle.

8. The salt of styphnic acid according to claim 1 for use in ignition systems which are ignited electrically.

9. The salt of styphnic acid according to claim 1, characterised in that the salt is the mixed salt potassium-calcium styphnate.

10. The salt of styphnic acid according to claim 1, characterised in that the salt is selected from the group consisting of basic calcium styphnate and basic potassium-calcium styphnate.

11. The salt of styphnic acid according to claim 1, characterised in that the salt is basic calcium styphnate.

12. The salt of styphnic acid according to claim 1, characterised in that the salt is basic potassium-calcium styphnate.

13. The salt of styphnic acid according to claim 1, characterised in that the salt is potassium-calcium styphnate and contains 12 to 14 wt. % potassium and 6 to 8 wt. % calcium.

14. The salt of styphnic acid according to claim 1, characterised in that the salt is basic potassium-calcium styphnate and contains 11 to 13 wt. % potassium and 11 to 13 wt. % calcium.

15. A process for the preparation of potassium-calcium styphnate according to claim 9, characterised in that calcium nitrate is added to a potassium styphnate solution.

16. A process for the preparation of basic calcium styphnate according to claim 11, characterised in that alkali hydroxide is added to a calcium styphnate suspension.

17. A process for the preparation of basic potassium-calcium styphnate according to claim 12, characterised in that alkali hydroxide is added to a potassium-calcium styphnate suspension.

18. The process for the preparation of potassium-calcium styphnate according to claim 15, characterised in that a stoichiometric quantity of calcium nitrate is added to the potassium styphnate solution.

19. The salt of styphnic acid according to claim 1, characterized in that the salt has a decomposition temperature of approximately 335° C.

* * * * *